United States Patent
Ettwein et al.

(10) Patent No.: US 8,808,168 B2
(45) Date of Patent: Aug. 19, 2014

(54) INSTRUMENT WITH SELF-UNLOCKING ADJUSTMENT WHEEL

(75) Inventors: Pierre Ettwein, Schaffhausen (CH); Marcel Jaeggli, Winterthur (CH); Elizabeth Jaeggli-Ott, legal representative, Winterthur (CH); Martin Klumpp, Tuttlingen (DE); Rolf Fuellemann, Andelfingen (CH)

(73) Assignee: Storz Endoskop Produktions GmbH (DE)

( * ) Notice: Subject to any disclaimer, the term of this patent is extended or adjusted under 35 U.S.C. 154(b) by 634 days.

(21) Appl. No.: 12/708,607

(22) Filed: Feb. 19, 2010

(65) Prior Publication Data
US 2011/0088498 A1      Apr. 21, 2011

(30) Foreign Application Priority Data
Feb. 20, 2009   (DE) .................. 10 2009 011 434

(51) Int. Cl.
*A61B 1/00*     (2006.01)
*A61B 1/005*    (2006.01)
*A61B 1/008*    (2006.01)

(52) U.S. Cl.
CPC ............. *A61B 1/0051* (2013.01); *A61B 1/0052* (2013.01); *A61B 1/0053* (2013.01); *A61B 1/0057* (2013.01); *A61B 1/008* (2013.01)
USPC .......................... 600/148; 600/149

(58) Field of Classification Search
CPC .. A61B 1/0051; A61B 1/0052; A61B 1/0053; A61B 1/0057; A61B 1/008
USPC ................. 600/139, 141, 142, 144, 146–150
See application file for complete search history.

(56) References Cited

U.S. PATENT DOCUMENTS

| 4,207,873 | A | * | 6/1980 | Kruy ............................ 600/146 |
| 4,461,282 | A | | 7/1984 | Ouchi et al. |
| 5,575,755 | A | * | 11/1996 | Krauter et al. ............... 600/148 |
| 5,782,147 | A | * | 7/1998 | Chaconas et al. ............. 81/63.1 |
| 5,888,192 | A | | 3/1999 | Heimberger |
| 6,216,563 | B1 | * | 4/2001 | Hsieh ........................... 81/63.2 |
| 6,551,239 | B2 | | 4/2003 | Renner et al. |
| 2002/0165484 | A1 | | 11/2002 | Bowe |
| 2007/0255102 | A1 | | 11/2007 | Maruyama |
| 2008/0007141 | A1 | * | 1/2008 | Deck ........................... 310/328 |

FOREIGN PATENT DOCUMENTS

| DE | 2917465 A1 | 12/1979 |
| DE | 3729131 C1 | 3/1989 |
| DE | 19650721 A1 | 6/1998 |
| DE | 19924440 A1 | 12/2000 |

OTHER PUBLICATIONS

European Search Report; Application No. EP 10 15 3780; Apr. 29, 2010; 4 pages.

* cited by examiner

*Primary Examiner* — Alireza Nia
(74) *Attorney, Agent, or Firm* — St. Onge Steward Johnston & Reens LLC (57) ABSTRACT

An instrument comprises a headpiece at a proximal end, a shaft connected to said headpiece, said shaft can be deflected at least in a distal end area thereof. A deflection mechanism is provided for deflecting said shaft. Said deflection mechanism has control wires and a control element for controlling a deflection movement of said deflection mechanism. A lock is provided for locking said deflection mechanism. Said lock has a catch mechanism connected to said control element in such a way that said catch mechanism, without actuation, is automatically forced into a locking position and a movement of said control element first opens said catch mechanism and only then permits a deflection of said shaft. A release of said control element in any position of said deflection mechanism causes an enforced locking by said catch mechanism in said position.

17 Claims, 7 Drawing Sheets

INSTRUMENT WITH SELF-UNLOCKING ADJUSTMENT WHEEL

BACKGROUND OF THE INVENTION

The invention relates to an instrument with a proximal headpiece, with a shaft that can be deflected at least in the distal end area via a deflection mechanism, with a control element via which deflection movements of the shaft can be controlled by movement of control wires of the deflection mechanism, and with a lock for locking the deflection mechanism.

Such an instrument is known from DE 37 29 131 C1.

Such instruments are now in widespread use.

One field of use are medical instruments. Endoscopic instruments used for this purpose have a shaft portion that can be angled, at least at the distal end area.

It is in this way possible to introduce the shaft initially in an elongate state into a cavity of a living body. This can be done, for example, via a trocar or trocar sleeve inserted into a body or by way of natural orifices of the body, for example the mouth, the anus or urethra. The shaft can be deflected laterally within the cavity, such that, for example in the case of endoscopes, views can be gained to either side of the rectilinear direction. The shafts themselves can be of a rigid or flexible design, the crucial point being that the distal end area can be deflected. In the case of instruments serving purely as endoscopes, this provides an all-round view within the body cavity. If operating instruments, for example a needle holder, are mounted at the distal end, it is also possible to perform manipulations, e.g. suturing procedures, at locations within the cavity that cannot be reached by a rectilinear instrument.

A further field of use lies in particular in endoscopes used to inspect technical equipment.

One field of use is the inspection of structural parts that are difficult to access, e.g. the rear ends of the air vanes of aircraft turbines. By using deflectable endoscopes, such locations that are difficult to access can be inspected without dismantling the turbines.

Other fields of use are, for example, engine construction or bodywork construction, the latter case in particular requiring the inspection of cavity seals within hollow bodywork structures of complicated form.

Further technical fields of use are inspections of buildings or masonry.

The range of use of such instruments with deflectable shafts is becoming ever wider.

To permit the deflecting movement, a deflection mechanism is provided which is in most cases composed of control wires that are routed along the shaft and are connected to a control element at the headpiece.

For example, if the distal end is to be deflected in one plane away from the rectilinear orientation, two diametrically opposite control wires are provided. To permit deflection, one of the two control wires is now pulled in and the diametrically opposite control wire is pushed out, as a result of which the flexible end area of the shaft is curved or bent outwards in one plane. Such a control element can, for example, have a reel or roller on which the two control wires are secured. Rotation of the reel by the control element causes one control wire to be unwound in one direction, while at the same time the other control wire is reeled in. In the opposite direction of rotation, exactly the reverse procedure takes place.

It is thus possible for the deflectable area of the shaft to be deflected through almost 180° to both sides of the longitudinal axis.

In further developments, the deflection mechanism has two such pairs of control wires, which are arranged offset from each other by 90°, such that the deflectable area of the shaft can be deflected in two planes orthogonal to each other. It has become established practice to provide two control elements that operate independently of each other, as is known from DE 199 24 440 A1, for example. A combination of both movements permits the positioning of the distal end on a sphere surface.

It has now been observed in practical application that, after the deflection, a relatively strong restoring moment acts on the shaft, and this tends to bring the deflected shaft back to a more or less rectilinear state. In a bent flexible shaft, the outer envelope is compressed on one side and stretched like a rubber sheet on the other side. This results in relatively strong restoring forces. If the control wires are made of relatively stiff wire, restoring forces also occur upon deflection, that is to say bending, of the wires.

To avoid unwanted restoring of the deflected bent shaft, locks were developed that lock the deflected shaft against return from a defined position of deflection.

In addition to the deflection mechanism, it was thus also necessary to provide a locking mechanism via which the shaft can be locked against return from a respective position of deflection.

In DE 37 29 131 C1 mentioned at the outset, this is achieved by a combined brake lever and control lever. The lever, whose central rotation axle is connected to a reel on which the control wires can be wound and unwound, constitutes the control element of the deflection mechanism. If the shaft has been deflected into a defined position by means of the control lever, the lever has to be turned in another direction in order thereby to actuate a brake mechanism, which is designed to prevent restoring of the deflected area, i.e. is designed to block this movement. However, a certain amount of movement back and forwards for fine correction is still possible as before.

If the shaft is to be moved to another position of deflection or is to be made rectilinear again, the combined brake lever and control lever has to be moved in one direction to initially release the brake mechanism and then has to be moved in another direction in order to move the control wires of the deflection mechanism.

This is disadvantageous in the sense that different directions of movements and different manipulations have to be performed using one and the same control element, in order to be able to carry out the different procedures, namely, on the one hand, actuation of the deflection mechanism and, on the other hand, actuation of the brake mechanism.

In a starting position, the brake mechanism is free, and the deflection mechanism can now be actuated by the lever. The lever then has to be moved deliberately in another direction in order to activate the brake mechanism.

This is ergonomically unfavourable, requires a high level of attention and poses the danger of the deflected shaft moving out of position if the brake mechanism is not correctly actuated.

Moreover, the operator does not immediately know whether the lever is in a position in which it can be turned in order to actuate the deflection mechanism, or whether it is already in the brake function, since for this purpose it only has to be lifted a few millimeters from the rotation position.

This poses the problem that if pressure is inadvertently applied to the lever, the brake function is released and the deflected shaft moves.

This is fatal in the medical field in particular, for example if a surgical intervention is being performed with the deflected end.

It is, therefore, an object of the present invention to develop an instrument of the kind mentioned at the outset such that the control and in particular the locking and unlocking can be carried out safely, particularly using one hand.

SUMMARY OF THE INVENTION

According to the invention, this object is achieved by an instrument comprising a headpiece at a proximal end, a shaft connected to said headpiece, said shaft can be deflected at least in a distal end area thereof, a deflection mechanism for deflecting said shaft, said deflection mechanism having control wires and a control element for controlling a deflection movement of said deflection mechanism via said control wires, and a lock for locking said deflection mechanism, wherein said lock has a catch mechanism connected to said control element in such a way that said catch mechanism, without actuation of said control element, is automatically forced into a locking position, and wherein a movement of said control element first opens said catch mechanism and only then permits a deflection of said shaft, and wherein a release of said control element, in any position of said deflection mechanism, causes an enforced locking by said catch mechanism in said position.

These measures have a number of advantages.

By providing a catch mechanism, a mechanically simple and effective means is created for locking the shaft against undesired deflection movements.

This catch mechanism is brought positively, i.e. automatically, into the locking position when the control element is not moved or when it is released after a movement. The starting state or normal state is such that the catch mechanism is located in its locking position.

This has the advantage, for example for storage, for transport or for preparation of handling measures, that the shaft is in a clearly defined orientation from which it cannot move without the catch mechanism being released. It is thus possible to handle the flexible deflectable area, in this locked position, as a rigid shaft.

It is only when the control element is actuated, i.e. moved, that the catch mechanism initially opens and, upon further movement, a deflection of the shaft is possible via the deflection mechanism. When the control element is released, specifically in any position of the deflection mechanism, a direct and immediate movement into the locking position is enforced. The operator does not have to move the control element to some other position and instead simply releases it, as a result of which the catch mechanism immediately re-engages in the locking position. Basically, the operator has to move the control element only in one direction in order initially to release the catch mechanism and thereafter to effect the deflection movements. After it has been released, the catch mechanism is brought back immediately to its locking position, without further deflection movements being possible.

Therefore, the operator no longer has to know or ascertain whether the control element is in a state in which it has a locking action or permits a deflection movement, since it is always located automatically and positively in the locking state. Upon each movement of the control element, the locking action is always first released, and only then can the deflection movement take place, irrespective of whether this is a movement to deflect a rectilinear shaft or to bring a previously deflected shaft back to the rectilinear position.

In another embodiment of the invention, the catch mechanism has a row of teeth into which a movable detent can be introduced with a positive locking action, which detent can be moved out of the locking engagement by the control element.

This measure has the advantage that this positive control can be effected by mechanically simple but robust means.

In another embodiment of the invention, the detent is pretensioned resiliently in the direction of the row of teeth.

This measure has the advantage that the detent is permanently pretensioned in the direction of the locking engagement with the row of locking teeth and would therefore seek to move in this direction in whatever state. This can be achieved by the detent being subjected to the force of a spring, or by the detent itself being made of resilient material or being suitably shaped and inherently pretensioned.

This contributes to a simple mechanical structure and to consistently reliable handling.

In another embodiment of the invention, the row of teeth and the detent are shaped in such a way that a movement of the detent along the row is blocked, and only a movement of the detent out of the row permits a movement.

This measure has the advantage that, in the engaged state, a relative movement along the row of teeth is effectively blocked. It is only when the detent is moved out of the row of teeth that a movement of the deflection mechanism can take place. Particularly in connection with the aforementioned measure of the pretensioned detent, it is possible, with mechanically simple and robust structural parts, to create the conditions for ensuring, on the one hand, an engagement or locking that is automatically always closed when the detent is released, and for ensuring, on the other hand, that even very slight movements of the control element suffice to move the detent out of the locking engagement with the row of teeth.

In another embodiment of the invention, the teeth and the detent are shaped in such a way that the detent can be moved along the row of teeth when a predetermined counter-force is overcome.

By adaptation of the shape between teeth and detent and of the corresponding pressing force of the detent on the row of teeth, it is possible to ensure that the locking action along the row of teeth is subject to considerable forces and that the detent is disengaged only when a defined counter-force is overcome. It is then possible for the detent to run over the row of teeth. However, it is at all times ensured that, when the control element is released, the detent immediately and automatically engages in the next possible gap between two teeth and in this way once again provides the locking engagement.

In another embodiment of the invention, the teeth and the detent are shaped in such a way that a movement of the detent is blocked in one direction of said row of teeth but is possible in the opposite direction when said counter-force is overcome.

This possibility has the advantage of permitting particularly reliable deflection or control in two directions or opposite directions.

If a shaft is imagined in a rectilinear orientation, it can be deflected in one plane, for example to the left or to the right, using a pair of wires. If the shaft is to be deflected to the left, it is possible, by means of the aforementioned measure, to completely release the locking action in this direction. The detent can run over the row of teeth in the opposite direction. If each direction of movement is assigned a row of teeth, a detent can run over these in one direction, whereas, in the opposite direction, the detent first has to be lifted from the row. A second detent with opposite characteristics provides locking in the direction in which the other detent can travel over the teeth, and vice versa.

In another embodiment of the invention, the detent has an asymmetrical detent tooth which blocks the movement of the detent in one direction by positive locking and which can run over the row of teeth in the other direction, when said counterforce is overcome.

This measure has the advantage that the two-directional movement is made possible by structurally simple and mechanically robust measures.

In another embodiment of the invention, two detents are present, of which a first detent provides locking in a first direction along the row of teeth, and of which a second detent provides locking in a second direction opposite to the first direction, and the control element, upon movement in the first direction, releases the first detent from locking engagement and, upon movement in the second direction, releases the second detent from said locking engagement.

This measure has the advantage that, if the control element is not moved, both detents are in locking engagement and thus provide locking in both directions of movement.

If the control element is now moved in one direction, the detent that blocks this direction of movement is the one first brought out of the locking position. The other detent can run over the row of teeth when a certain pressing force is overcome.

If the control element is moved in the opposite direction, the detent blocking this direction is first of all lifted out of the row of teeth, such that the movement in this direction is made possible, in which case the other detent then runs over the row of teeth, again when a certain pressing force is overcome.

By structurally simple measures, it is here ensured that, in the direction blocked by a detent, it is this detent that is first lifted out of the locking engagement by the control element when the latter is moved in this direction, while the other detent can still run over the row of teeth in this direction when a certain pressing force is overcome. Thus, one of the detents is always connected to the row of teeth under a certain pressing force, so as to ensure that this detent comes into locking engagement directly after the control element is released.

In another embodiment of the invention, the row of teeth is designed as a pinion around which the detents are arranged as a pivotable single-arm lever.

This measure has the advantage of permitting a very compact structure. The pinion makes available an endless path of teeth, and suitably shaped detents or a suitable number of detents can then be arranged around the outer face of the pinion.

In another embodiment of the invention, the pinion has two rows of teeth, teeth of a first row can engage with a first detent and teeth of a second row can engage with a second detent.

These measures have several advantages. First, each row of teeth can be optimally adapted to the detent with which they engage. Mostly, the locking element of the detent is a detent tooth which acts with the teeth of the pinion in that the detent tooth locks absolutely in one turning direction of the pinion, but the detent tooth can run over the row of teeth in the opposite direction. Due to the fact that for each detent an individual row of teeth is provided, the geometry of the teeth of one row can be adapted optimally to the geometry of the detent tooth. As a result, the free motion when closing the catch mechanism can be diminished remarkably, since the row of teeth has to be adapted only to the detent tooth of one of the detents. Accordingly, the other row of teeth can be adapted optimally to the detent tooth of the other detent. As a result, in both turning directions of the pinion, only a very little free motion is present when closing the catch mechanism. This opens the possibility to arrange and to design the teeth asymmetrically, with the result that with small parts in one direction of turning of the pinion, an optimal catch action can be achieved, and in the opposite direction these teeth can be simply run over by the detent.

In a further embodiment of the invention, the pinion is assembled of two superposed pinion discs, each of which having a row of teeth which are directed oppositely to one another.

This measure has the advantage that both pinion discs can first be manufactured as individual parts and can then be assembled to a double-pinion with two rows of teeth. It is thereby possible to manufacture two identical pinion discs and to superpose it inversely. It is also possible to provide at one pinion disc a mounting feature via which it can be assembled with the other pinion in a predetermined orientation. This mounting feature may be a flange upstanding from one pinion disc, onto which flange the other pinion disc can be sliding. This opens different ways of mounting the pinion.

In another embodiment of the invention, the control element is designed as a rotary wheel, which is rotatable about the stationary pinion.

This measure has the advantage that the control element has a very favourable design from the ergonomic point of view and is easy to grip, and that the locking forces can be diverted or transferred to the instrument via the stationary pinion.

In another embodiment of the invention, a driver is arranged on the rotary wheel, which driver, in each position of rotation, engages with one of the detents and in so doing releases it from the locking engagement and keeps it released for as long as the rotary wheel exerts the force required for this on the detent.

This measure has the advantage that the deflection mechanism can be moved, or if appropriate can also be corrected, as long as this locking detent is maintained out of engagement by the rotary wheel. This state of course starts when the rotary wheel is gripped and moved. When a defined position of deflection of the shaft has been reached, the rotary wheel can continue to be held in the hand, that is to say counter to the restoring force of the deflected shaft, in order to optionally check the exact position of deflection. After the rotary wheel is released, the detent then immediately engages the row of teeth and blocks further movement. If a large deflection lever is chosen, that is to say long detents, and a small tooth engagement lever, the mechanism runs particularly smoothly. Jamming is also avoided.

In another embodiment of the invention, the released detent is pressed by the driver against an abutment on a driver disc, said driver disc being connected with a force fit to the deflection mechanism.

This measure has the advantage that the rotation movement of the rotary wheel is first used to disengage the locking detent from the locking engagement, without a deflection of the shaft thus already taking place. It is only after the driver presses the detent against an abutment on a driver disc that the latter is rotated, and the rotation movement is then transferred to the deflection mechanism. In this state, the operator can monitor or estimate the degree of deflection on the basis of the extent to which the rotary wheel is pivoted. He can then establish, if appropriate without direct visual control, how much the deflectable end has been deflected.

In another embodiment of the invention, two such deflection mechanisms are present in an instrument whose shaft can be deflected independently in two planes.

This measure has the advantage that in such devices, and in accordance with the underlying concept of the invention, these movements can be performed reliably and in an ergonomically simple way in both deflection planes.

In another embodiment of the invention concerning this latter embodiment, two rotary wheels are provided which are placed on each other and are held mechanically on each other, but which permit actuation of each of the rotary wheels independently of the other.

This measure has the advantage that the deflection movements to the left and right or upwards and downwards can be performed in the same way by the two rotary wheels.

It will be appreciated that the aforementioned features and those still to be explained below can be used not only in the cited combinations but also in other combinations or singly, without departing from the scope of the present invention.

BRIEF DESCRIPTION OF THE DRAWINGS

The invention is described and explained in greater detail below on the basis of a number of illustrative embodiments and with reference to the attached drawings, in which.

DETAILED DESCRIPTION OF PREFERRED EMBODIMENTS

Figures 1, 2:
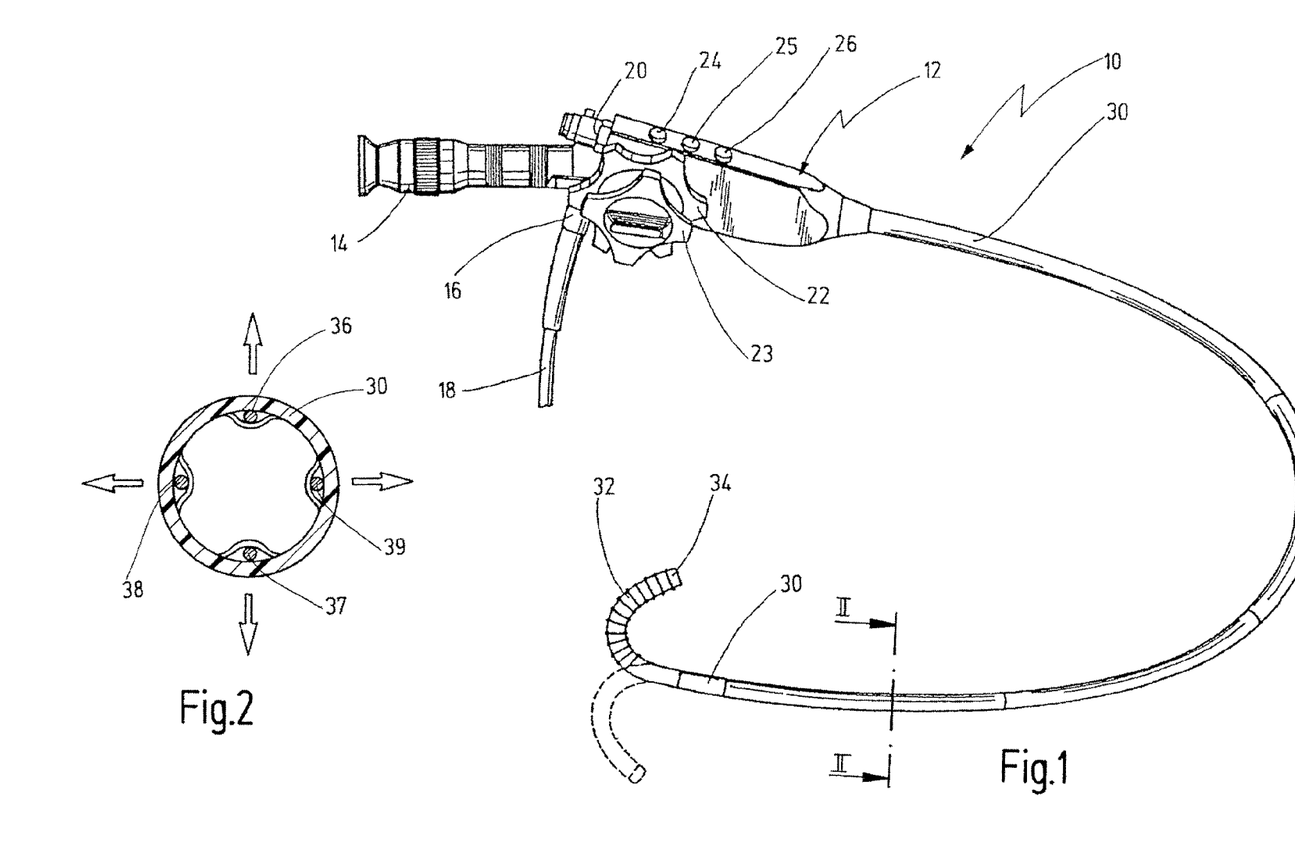
FIG. 1 shows a perspective view of an instrument with a shaft, the distal end area of which can be deflected.
FIG. 2 shows a cross section along the line II-II in FIG. 1.

A flexible endoscope shown in FIGS. 1 and 2 is designated in its entirety by reference number 10. The flexible endoscope 10 is an instrument used in the medical field, for example for examining the digestive system of large animals such as cattle or horses via the rectum.

This instrument does not differ in principle from a flexible endoscope used in the technical sector, for example for inspecting the rear face of turbine blades of a turbine engine for an aircraft.

The endoscope 10 has a headpiece 12. An eyepiece 14 protrudes from the proximal end of the headpiece 12. A laterally protruding connector piece 16 serves for the attachment of a cable 18 that can contain leads for illumination, irrigation, insufflation, suction or the like. Another connector piece 20 extending more or less in the direction of the eyepiece 14 is provided to allow other instruments, for example forceps, snares or the like, to be inserted into the instrument. Two control elements 22 and 23 in the form of rotary wheels are arranged on the side of the headpiece 12 and can be used to adjust the viewing direction of the endoscope, as will be explained below. In the area of the headpiece 12, there are also switches 24, 25, 26, via which various functions can be controlled, for example suction, irrigation or the like.

An elongate, flexible shaft 30 continues from the headpiece 12 and, in the illustrative embodiment shown, has a length of approximately 1 m. The shaft 30 is produced from a flexible multi-layer structure, which permits curving and bending of the shaft 30, as is shown in FIG. 1. A distal end area 32 has even greater flexibility than the shaft 30 in order to ensure that the distal end area 32 can also be deflected still further through more than 180° in a semicircle shape. This is possible in the first instance in one plane, as is shown in FIG. 1, that is to say in the plane of the drawing. In addition, the distal end area 32 can also be deflected perpendicularly with respect to the plane, that is to say upwards and downwards from this plane. Both deflection movements can be performed simultaneously, as a result of which the distal endpiece 34 (also called beak) moves on a surface of a sphere.

As can be seen from the cross-sectional view in FIG. 2, two pairs of control wires 36, 37 and 38, 39, respectively, are arranged in the inside of the shaft 30. These control wires are made of relatively stiff wire. The pair of control wires 36, 37 are connected to the control element 22 on the headpiece 12. When the control element 22 is turned, for example in the clockwise direction, the control wire 36 is wound onto a roller operatively connected to the control element 22, and at the same time the control wire 37 is unwound. Instead of a roller, a chain drive with a toothed wheel may also be present. In this way, an upward deflection of the distal end area 32 takes place. If the control element 22 is turned in the opposite direction, the control wire 37 is wound up and the control wire 36 is unwound, such that the distal end area 32 is then deflected downwards, as is indicated by an arrow.

The control wires 38 and 39 are correspondingly connected to the control element 23. If the latter is turned in the clockwise direction, the wire 38 is wound up and the wire 39 is unwound and the distal end area 32 is deflected to the right, as is indicated in FIG. 1 by solid lines. Accordingly, a rotation of the control element 23 in the opposite direction then causes a deflection to the left, as is shown by the broken lines. These structural parts thus constitute a deflection mechanism for the distal end area 32.

To ensure that the deflected distal end area 32 remains in a defined position of deflection, a catch mechanism is provided by which the deflection mechanism is held in this position.

Figure 3:
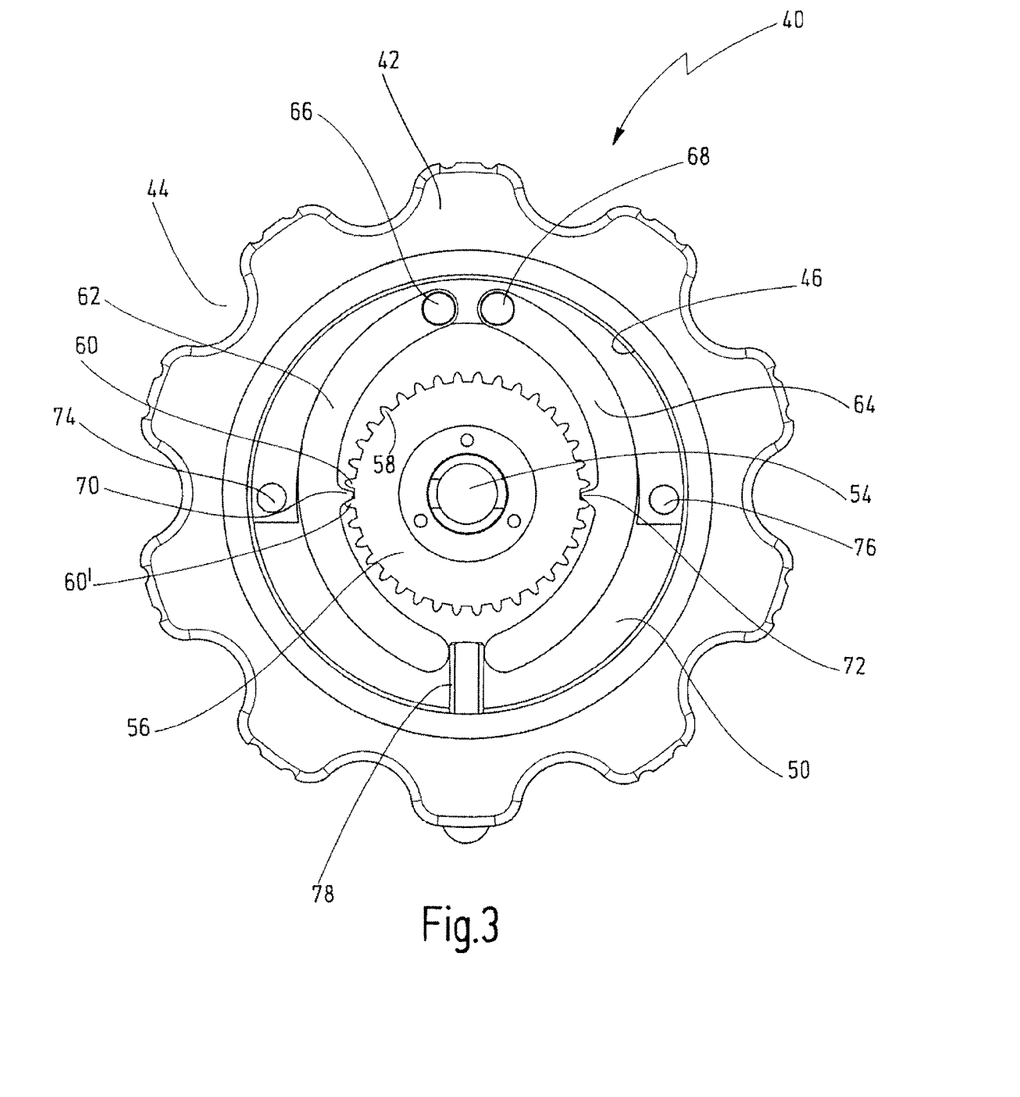
FIG. 3 shows a greatly enlarged side view of a rotary wheel of the instrument from FIG. 1.

The control element 40 shown in FIG. 3 corresponds to the first, inner control element 22 shown in FIG. 1 and contains such a catch mechanism.

As can be seen from FIG. 3, the control element 40 is in the form of a rotary wheel 42, with a plurality of finger recesses 44 provided on the outer face thereof. As can be also seen in particular from the partial cross-sectional view in FIG. 14, the control element 40 is composed of an annular body 46.

Figure 14:
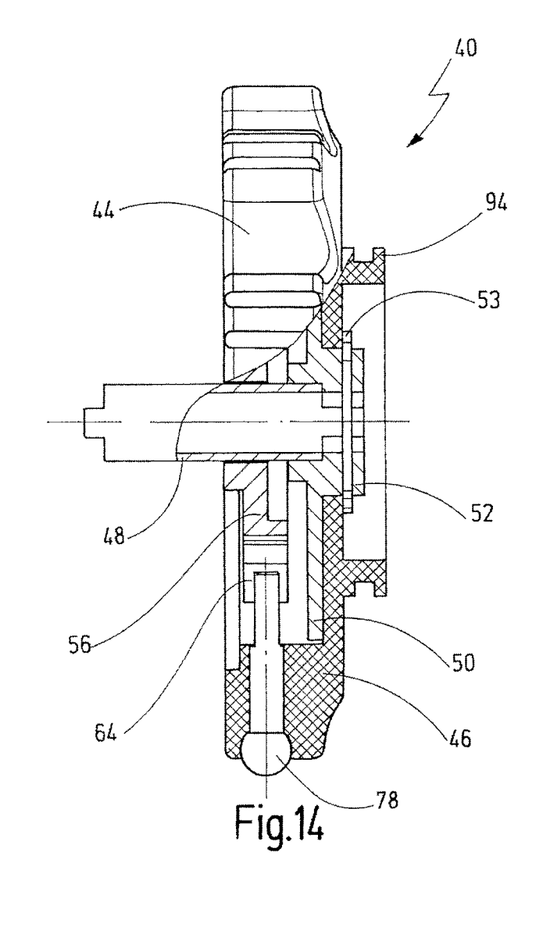
FIG. 14 shows a side view of the rotary wheel from FIG. 3, partially in cross section.

This annular body 46 is pushed onto an assembly flange 52 of a driver disc 50 and is held firmly thereon by a securing means 53. The driver disc 50 itself sits on a central shaft 48. A rigid axle 54 extends through the shaft 48 and carries a pinion 56 which, in the view in FIG. 14, is arranged on the left-hand side, i.e. the side directed towards the headpiece 12 of the instrument 10. The rigid axle 54 and thus also the pinion 56 secured thereon are likewise connected fixedly and immovably to the headpiece 12 of the instrument 10.

Two detents 62 and 64 are mounted on that side of the driver disc 50 directed towards the headpiece 12, as can be seen in particular from FIG. 3. Each detent 62 and 64 is made from a bent metal strip, and they are mounted pivotably on journals 66 and 68 protruding from the driver disc 50. A detent tooth 70 protrudes from the detent 62, and a detent tooth 72 protrudes in mirror image from the detent 64, in each case in the direction of respective teeth 60, 60' of the pinion 56.

Figure 4:
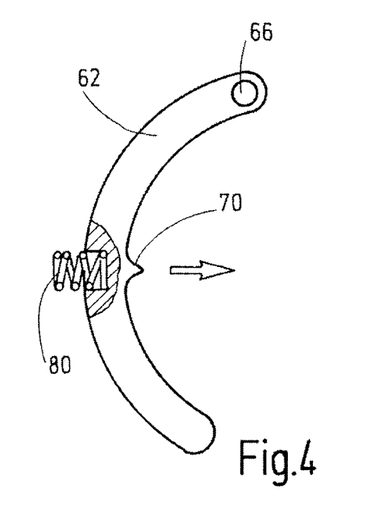
FIG. 4 shows a structural part, namely a detent, of the rotary wheel shown in FIG. 3.

The detent 62 is shown in greater detail in FIG. 4. It will be seen from this that a spring 80 sits in a cutting (not described in any more detail here), one end of the spring 80 being received in the recess, and the other end bearing on a respective pin 74 or 76, which likewise projects from the driver disc 54.

By means of these springs 80, the detents 62 and 64 are each pivoted about the journals 66 and 68, respectively, such that the detent teeth 70, 72 thereof mesh in the pinion, that is to say between corresponding teeth 60, 60' of the row of teeth.

Figure 5:
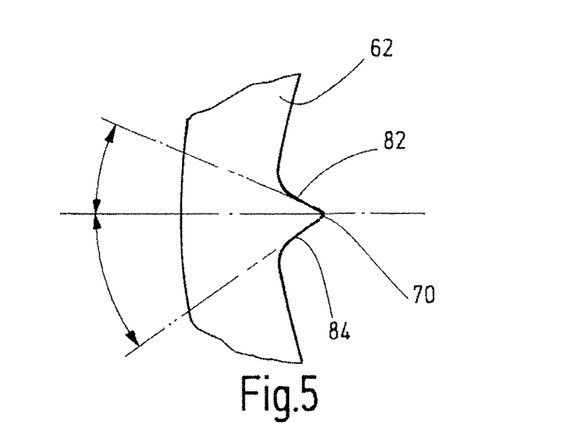
FIG. 5 shows a greatly enlarged detail of a detent tooth of the detent.

It will be seen from the enlarged view in FIG. 5 that the detent tooth 70 has two flanks 82, 84 of different steepness. The flank 82 is steeper than the flank 84 when seen in relation to the central longitudinal axis indicated by broken lines.

Figure 6:
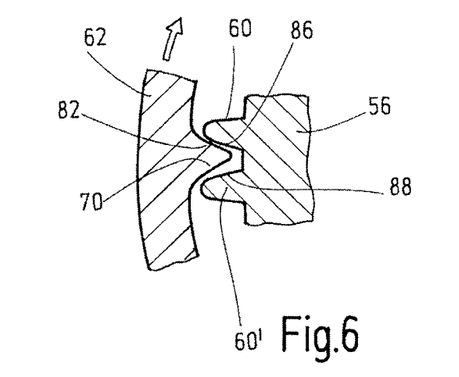
FIG. 6 shows a cross-sectional detail of the detent from FIG. 4, of which the detent tooth is engaged between two teeth of a row of teeth.

It will be seen from FIG. 6 that the flanks 86 and 88 of the teeth 60 and 60', respectively, correspond approximately to those of the flank 82.

The view in FIG. 6 corresponds to the situation of the detent 62 in FIG. 3.

Should the detent 62 be moved in the direction of the arrow as shown in FIG. 6, this movement is blocked by the flank 82 of the detent tooth 70 and by the corresponding flank 86 of the tooth 60.

Figure 7:
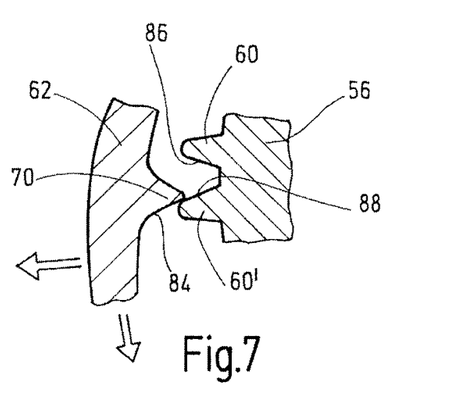
FIG. 7 shows a view, comparable to FIG. 6, in which the detent tooth is running over one tooth of the row of teeth.

FIG. 7 shows that, in the opposite movement of the detent 62, the shallower flank 84 can slide along the flank 88 of the tooth 60', with the detent 62 being moved in the direction away from the teeth 60, 60'.

In other words, the detent 62 is able to run over the pinion 56 in the direction indicated by the downward arrow in FIG. 7. However, because of the force of the spring 80, the detent 62 remains at all times in contact with the pinion 56. When the detent tooth 70 has traveled over the tooth 60', the detent tooth 70 engages back into the pinion, such that a situation such as the one shown in FIG. 6 is reached once again.

From the sequence of FIGS. 6 and 7, it will be seen that a movement of the detent 62 along the row 58 of teeth 60, 60' of the pinion 56 is blocked in one direction, whereas the detent can run freely over it in the opposite direction.

By virtue of the articulation on the journal 66, the detent tooth 70 can be moved out of engagement in the direction of elevation of the teeth 60, 60'.

Figure 8:
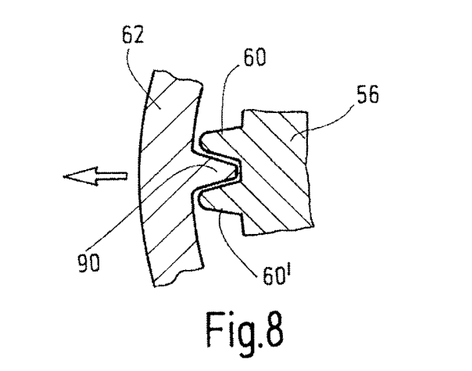
FIG. 8 shows a view, comparable to FIG. 6, of another illustrative embodiment of a detent tooth.

FIG. 8 shows a situation in which the geometry of the detent tooth 90 is configured such that its flanks are contoured in approximately the same way as the flanks 86 and 88 of the teeth 60 and 60'. In this configuration, a movement of the detent 62 is blocked in both directions along the row of teeth.

This blocking can be cancelled only if the detent 62 has first been completely lifted from the teeth 60 and 60'.

Figure 9:
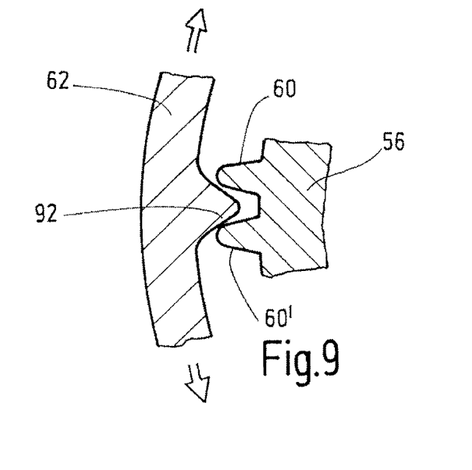
FIG. 9 shows a view, comparable to FIGS. 6 and 8, of another embodiment of a detent tooth.

FIG. 9 shows a situation in which the detent tooth 92 is configured such that it has two relatively shallow flanks corresponding to the flank 84.

In this case, the detent tooth 92 engages between the teeth 60 and 60' of the pinion and initially blocks a lengthways movement between detent 62 and pinion. However, if the force acting on the detent 62 is so great that the pressing force is overcome by the spring 80, the detent tooth 92 is able to run over the teeth 60, 60' of the pinion 56 in both directions.

In all cases, by means of the corresponding detent tooth 70, 90 or 92 engaging between the teeth 60, 60', a locking action is brought about between the detent 62 and the pinion 56.

In all these locking states, the rotary wheel 40 cannot be turned about the pinion 56. To do so, the corresponding detent tooth has to be moved out from between the teeth 60, 60', as has been described above in connection with FIGS. 6, 7, 8 and 9.

When the above-described catch mechanism between detent 62 and pinion 56 is released, the rotary wheel 42 can be moved further and, in this way, the distal end area 32 can then be deflected via the deflection mechanism.

The embodiment of the catch mechanism discussed above in connection with FIGS. 4 to 7, and shown in principle in FIG. 3, will now be described in greater detail with reference to the sequence of FIGS. 10 to 13.

FIG. 3 shows a starting position in which the shaft 30 is in a rectilinear orientation. Both detents 62 and 64 are engaged in the pinion 56. The two detents 62 and 64 curved in an arc shape extend, starting from the journals 66 and 68, in an arc around both sides of the pinion 56 and, at the sides opposite the journals, they bear on both sides on a driver pin 78 that protrudes radially from the outside through the annular body 46 of the rotary wheel 42.

Rotation in the clockwise direction is blocked because the steep flank 82 bears on the corresponding steep flank 86 of the tooth, as is indicated in FIG. 6. Because of the mirror-image configuration of the detent 64, a movement in the anticlockwise direction is blocked because, in this direction of movement, the steeper flank of the detent tooth 72 is in locking engagement with the corresponding tooth of the pinion 56.

Since both detents 62 and 64 are pretensioned by the corresponding springs 80 in the direction of the pinion 56, this locking is maintained without external action. In other words, this state is automatically reached and maintained.

Figure 10:
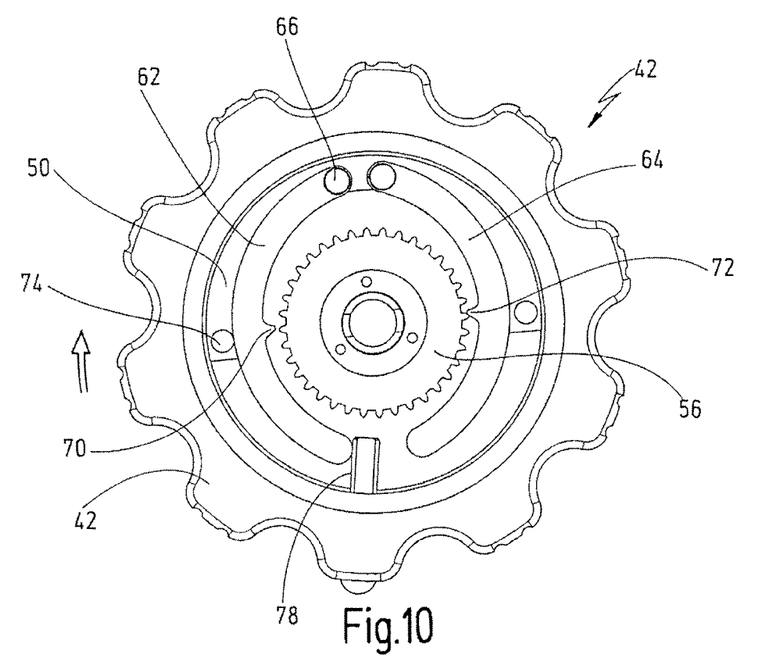
FIG. 10 shows a view, comparable to FIG. 3, in a position in which the rotary wheel has been turned slightly in the clockwise direction and a detent has just lifted out of the row of teeth.

If the rotary wheel 42 is now turned slightly in the clockwise direction, as is shown in FIG. 10, the driver pin 78 moves the detent 62 away from the pinion 56, as a result of which the locking engagement is cancelled.

The detent 62 can be pivoted radially outwards until it hits the pin 74 and closes there for a force fit between rotary wheel 40, driver pin 78, detent 62, pin 74 and driver disc 50.

From this point, the driver disc 50 thus also turns in the clockwise direction and then moves the control wires, as described above, and the distal end area of the shaft 30 is therefore deflected.

As can be seen from FIG. 10, the detent tooth 72 of the detent 64 runs in this direction with its shallow flank over the teeth 60, 60' of the pinion 56. The spring (not shown here) of the detent 64 presses the detent tooth 72 permanently into contact with the pinion.

Figure 11:
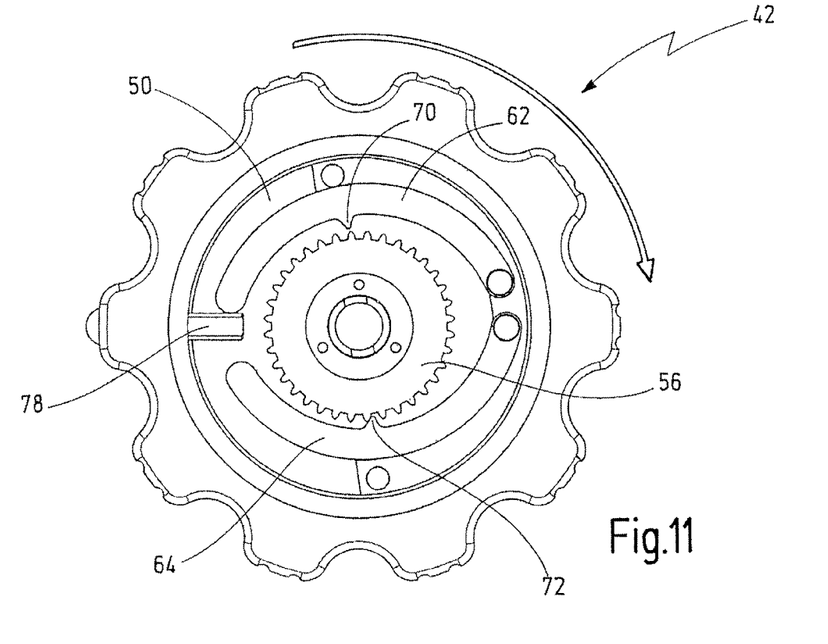
FIG. 11 shows a position, comparable to FIGS. 3 and 10, after the rotary wheel has been turned through 90° in the clockwise direction.

FIG. 11 now shows a situation in which the rotary wheel 42 has been turned through approximately 90° in the clockwise direction. This rotation has caused a pivoting of the distal end area 32 through 90° from the rectilinear orientation.

If the rotary wheel 42 in the position shown in FIG. 11 is now released, the force of the spring 80 presses the detent tooth 70 back into a free space between two teeth 60, 60' of the pinion. This takes place immediately, without the rotary wheel 42 being able to turn further, since the engagement of the detent 64 with the pinion 56 already affords a preliminary locking in this position. If, in this state of rotation, the tips of the teeth of detent 62 and pinion 56 were to contact each other, a slight rotation movement can take place, but one that no longer has any effect on the deflection. Clamping is impossible, since the force of the detent 62 is not exactly radial and instead has a tangential component because of its articulation, such that a positive engagement of the detent 62 takes place.

Figure 12:
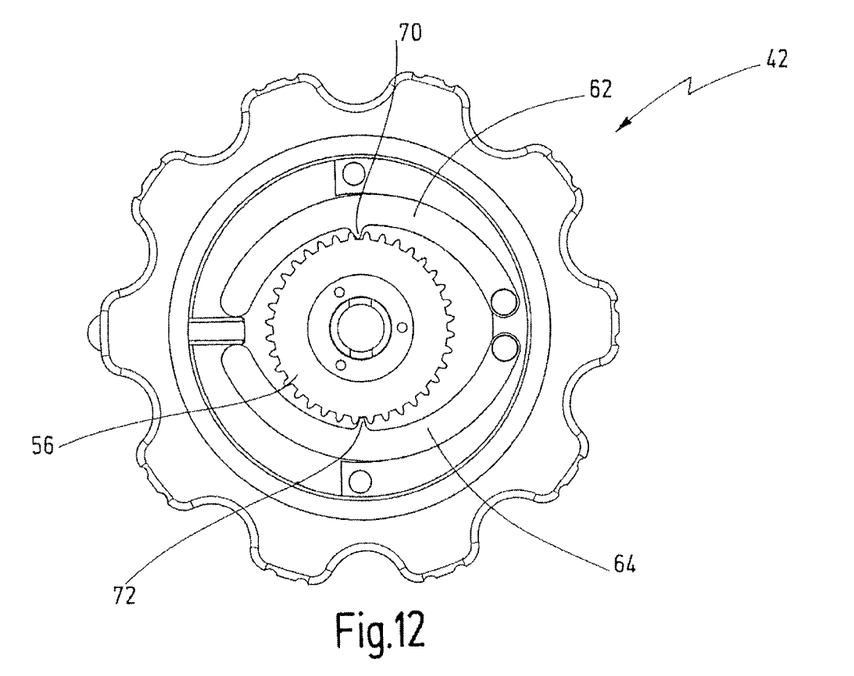
FIG. 12 shows a view, comparable to FIG. 11, after the rotary wheel has been released.

This state is shown in FIG. 12.

It will be seen from this that the locking action provided by the catch mechanism is always present, and also maintained, when the rotary wheel 42 is released. This is independent of the position of rotation, for example in the starting position shown in FIG. 3 or in the position of rotation shown in FIG. 12, where the distal end area 32 is deflected and considerable restoring forces act on the rotary wheel 42.

If the deflected distal end area 32 is to be moved back into the rectilinear position, the rotary wheel 42 is turned anti-clockwise from the position described in FIG. 12.

Figure 13:
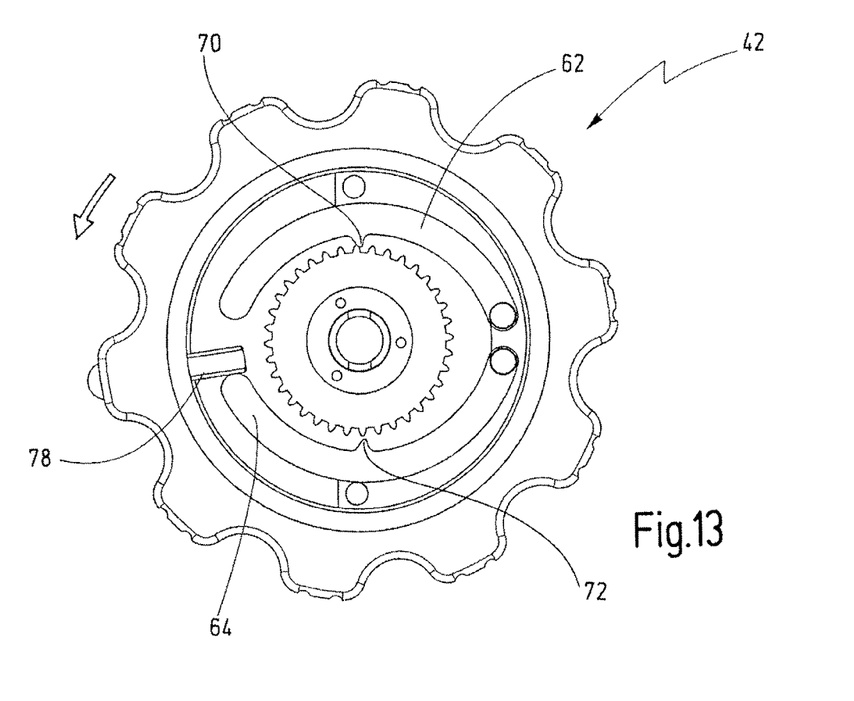
FIG. 13 shows a view, comparable to the view in FIG. 10, the rotary wheel having moved slightly in the anticlockwise direction from the view shown in FIG. 12.

It will be seen from FIG. 13 that the driver pin 78 then meets the other, opposite detent 64 and lifts the latter out of the locking engagement. In this position of rotation, the detent tooth 70 of the detent 62 can travel over the teeth of the pinion 56.

When the end area 32 is then once again in a rectilinear orientation for example, that is to say the position shown in FIG. 3 has been reached, the rotary wheel 42 can be released, and both detents 62 and 64 lock again.

A corresponding procedure occurs when, for example, the rotary wheel 42 is turned in the anticlockwise direction from the position shown in FIG. 3. The catch mechanism can thus be regarded as a catch mechanism that is self-unlocking in two directions. This procedure is ergonomic and also very simple to carry out from the tactile point of view, since the rotary wheel 42 can be gripped securely via the finger recesses 44, and manipulations have to be performed only in one defined direction of rotation by turning the rotary wheel 42, with the result that attention does not have to be paid as to whether a lock or catch is opened or closed, since it automatically closes when the rotary wheel 42 is released and is forcibly unlocked as soon as the rotary wheel 42 is turned.

FIG. 14 shows how the control element 40 described above is assembled.

The introduction described how, in many designs, a pivoting of the distal end area 32 of the shaft 30 in two different planes is desired.

Figure 15:
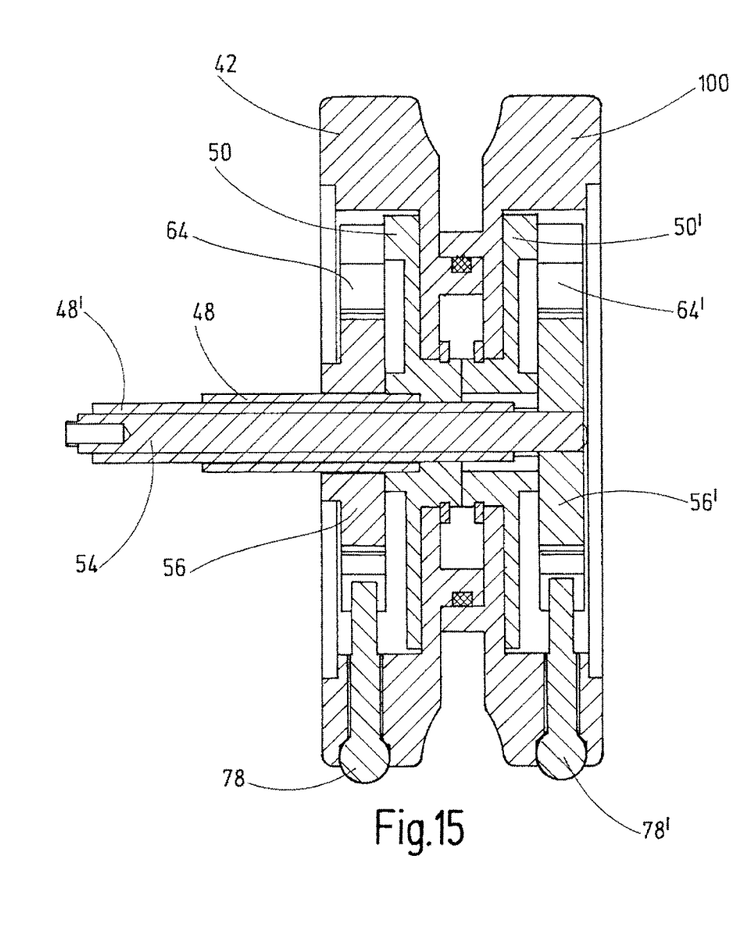
FIG. 15 shows a cross-sectional view in which a further rotary wheel is placed onto the first rotary wheel from FIG. 14.

For this purpose, as can be seen from FIG. 15, a second rotary wheel 100 corresponding to the rotary wheel 42 and approximately the mirror image thereof is mounted on the first control element 40 or rotary wheel 42. To do so, as can be seen from FIG. 14, an assembly flange 94 protrudes from the rotary wheel 40, and, as can be seen from FIG. 15, the rotary wheel 100 can be pushed onto this assembly flange 94 and held thereon. The rotary wheel 100 pushed on in this way is secured against falling off but can be rotated independently of the rotary wheel 42.

In this case, the central rigid axle 54 extends so far that it reaches into the second rotary wheel 100, such that the pinion 56' of this rotary wheel can also be assembled thereon. Here too, a corresponding driver disc 50' is once again provided, on which corresponding detents are assembled, of which the detent 64' is shown here.

A driver pin 78' is also provided here which extends between the two detents and, depending on the direction of rotation of the rotary wheel 100, lifts them and thus cancels the locking action. The rotary wheel 100 is mounted on a further shaft 48', such that this shaft 48' is then rotated when the correspondingly deflected detent of the rotary wheel 100 is positively locked. It will be seen from FIG. 15 that this shaft 48' extends inside the shaft 48 of the rotary wheel 42 and runs over the outside of the rigid axle 54. Thus, the other pair of control wires can be moved or controlled by the shaft 48'.

If the tooth geometry shown in FIG. 9 is chosen, then, when one detent is lifted by the driver pin 78, a corresponding pressing force of the other detent lying opposite has to be provided, such that this detent is in permanent contact with the pinion.

This structure can be chosen if the restoring forces by the deflected end area 32 are not very great.

Should these restoring forces be extremely great, or if extreme restoring forces act on the deflected distal end area because of manipulations, a tooth form such as the one in FIG. 8 may be considered.

However, it is then necessary to ensure that both detents are lifted upon rotation of the rotary wheel.

Two detents have been described hitherto as separate structural parts.

They can be made from spring steel and, by suitable assembly, can be tensioned on the pinion. The springs 80 can then be omitted.

The two detents can be produced as a single structural part, connected to each other in the area of the journals 66 and 68.

The underlying principle must always be satisfied, i.e. that the catch mechanism automatically closes after release of the rotary wheel but is freed with one and the same movement of the rotary wheel, as in the movement of the deflection mechanism.

Figure 16:
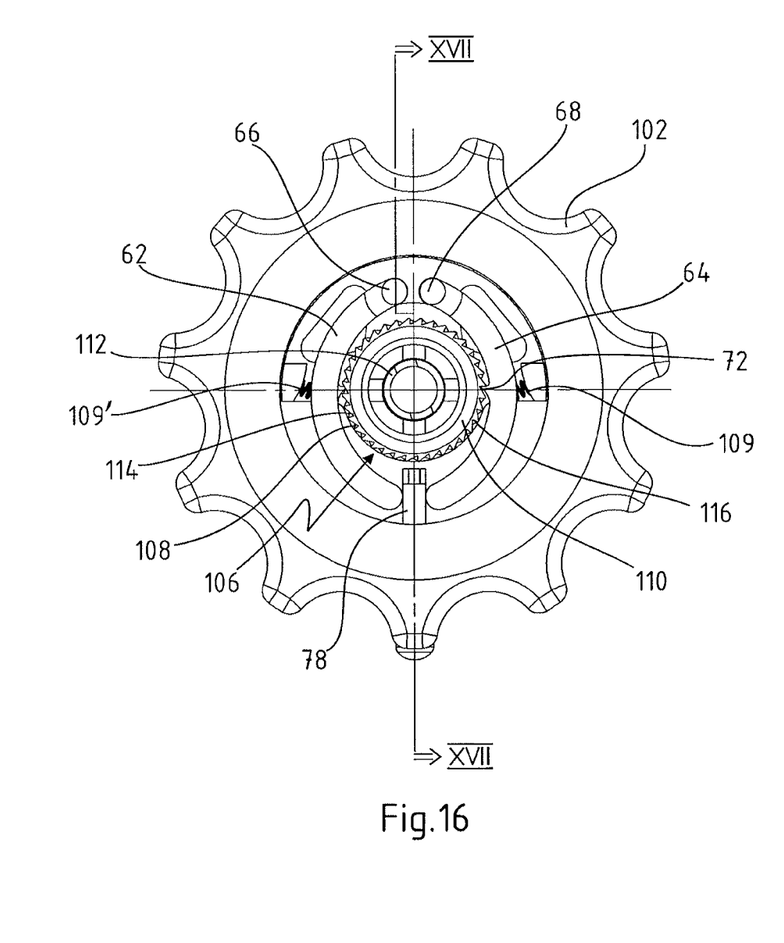
FIG. 16 shows a view, comparable to FIG. 3, of a further embodiment with a double-pinion.
Figure 17:
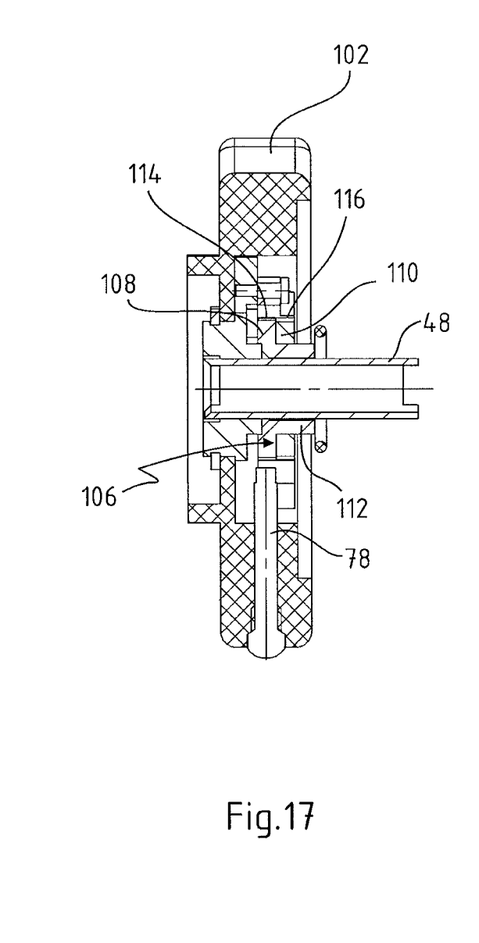
FIG. 17 shows a cross section along the line XVII-XVII in FIG. 16.

From FIGS. 16 and 17, a further embodiment of a control element in the shape of a rotary wheel 102 is shown. For similar or identical structural parts, which have already been described in the previous embodiment, the identical reference numerals are used.

The rotary wheel 102 is designed, as described in connection with FIG. 3, as an annular body which is pushed onto a driver disc and held firmly thereon by securing means. A pinion 106 is mounted on a central shaft 48 and is assembled of two superposed pinion discs 108 and 110.

The inner, or, in the view of FIG. 16, the lower first pinion disc 108, is provided with an upstanding flange 112 onto which the second pinion disc 110 is pushed.

The first pinion disc 108 has along its outer circumferential edge a first row of teeth 114 which are shaped asymmetrically.

The second pinion disc 110 has at its outer circumferential edge a second row of teeth 110, which are also asymmetrically, but they are oriented in the opposite direction.

The first row of teeth 114 of the first pinion disc 108 engages with a (not shown here) detent tooth of the first detent 62.

The second row of teeth 116 of the second pinion disc 110 engage with the corresponding asymmetrical detent tooth 72 of the second detent 64.

The two detents 62 and 64 are mounted on different levels for having its detent tooth engaging with its apparent row of teeth 114 and 116, respectively.

As can be seen from FIG. 16, the asymmetrical detent tooth 72 of the second detent 64 is designed in that it can run over the teeth 116, when viewed in clockwise direction, but catches counter-clockwise. A spring 109 provides that the second detent 64 is pushed against the teeth 116. Correspondingly, the opposite first detent 62 is pushed by a corresponding spring 109' against the row of teeth 114 arranged below in the view of FIG. 16. The second detent 64 catches in the opposite direction to the first detent 62.

With that embodiment, the functional principle is the same as described before. If the rotary wheel 102 is, for example, turned counter-clockwise, the driver pin 28 lifts the second detent 64 and its detent tooth 72 out of the locking engagement of the second row of teeth 116 against the force of the spring 109. This occurs almost without any free motion. Now, the rotary wheel 102 can be turned counter-clockwise. Thereby, the first detent 62 runs over the first row of teeth 114, and that against the force of the spring 109'.

If the rotary wheel 102 is given free, the spring 109 pushes the detent tooth 72 of the second detent 64 into the next gap between two neighbored teeth 116, and the mechanism is locked again.

The same applies for the opposite turning direction. In this case the driver pin 78 lifts the first detent 62 from the lower row of teeth 114 and the detent tooth 72 of the second detent runs over the teeth 116 of the second pinion disc 110.

The invention claimed is:

1. An instrument, comprising
a headpiece at a proximal end,
a shaft connected to said headpiece, said shaft can be deflected at least in a distal end area thereof,
a deflection mechanism for deflecting said shaft, said deflection mechanism having control wires and a control element for controlling a deflection movement of said deflection mechanism via said control wires, and
a lock for locking said deflection mechanism, wherein said lock has a catch mechanism connected to said control element in such a way that said catch mechanism, without actuation of said control element, is automatically forced into a locking position, and
wherein a movement of said control element in a direction first opens said catch mechanism and only then permits a deflection of said shaft and allows said deflection mechanism to move over its entire deflection range,
wherein a further movement of said control element in said direction deflects said deflection mechanism; and,
wherein a release of said control element in any position of said movement causes said locking mechanism to return to the locking position, thereby locking said deflection mechanism in a deflected position,
wherein said catch mechanism has a row of teeth into which a movable detent can be engaged with a positive locking action, which detent is moved out of an engagement with said row of teeth while moving said control element.

2. The instrument of 1, wherein said detent can be moved out of a locking engagement by said control element.

3. The instrument of claim 1, wherein said detent is pretensioned resiliently in a direction of said row of teeth.

4. The instrument of claim 3, wherein said row of teeth and said detent are shaped in such a way, that a movement of said detent along said row is blocked, and only a movement of said detent out of said row permits a movement of said deflection mechanism.

5. The instrument of claim 3, wherein said row of teeth and said detent are shaped in such a way that said detent can be moved along said row of teeth when a predetermined counterforce is overcome.

6. The instrument of claim 5, wherein said row of teeth and said detent are shaped in such a way, that a movement of said detent is blocked in one direction of said row, but it is possible in an opposite direction when said counterforce is overcome.

7. The instrument of claim 6, wherein said detent has an asymmetrical detent tooth which blocks said movement of said detent in one direction by positively locking and which can run over said row of teeth in an opposite direction when said counter-force is overcome.

8. The instrument of claim 1, wherein two detents are present, of which a first detent provides a locking in a first direction along said row of teeth, and of which a second detent provides a locking in a second direction opposite to said first direction, and said control element, upon movement in said first direction releases said first detent from locking engagement, and, upon movement in said second direction, releases said second detent.

9. The instrument of claim 8, wherein a respective other detent, which is not moved out of said locking engagement by said control element, can run over said row of teeth when a pressing force is overcome.

10. The instrument of claim 1, wherein said row of teeth is designed as a pinion around which said detent or said detents is or are arranged as a pivotable single-arm lever.

11. The instrument of claim 10, wherein said pinion has two rows of teeth, teeth of a first row can come into engagement with said first detent, and teeth of a second row can be brought into engagement with said second detent.

12. The instrument of claim 11, wherein said pinion is assembled of two superposed pinion discs, each of which having a row of teeth which are directed oppositely to one another.

13. The instrument of claim 10, wherein said control element is designed as a rotary wheel, which is rotatable about said pinion which is stationary.

14. The instrument of claim 13, wherein a driver is arranged on said rotary wheel, said driver, in each direction of rotation of said rotary wheel, engages with a detent and in doing so releases it from a locking engagement and keeps it released for as long as said rotary wheel exerts a force required for this on said detent.

15. The instrument of claim 14, wherein said released detent is pressed by said driver against an abutment on a driver disc, said driver disc being connected to said deflection mechanism via a force fit.

16. The instrument of claim 1, wherein said shaft can be deflected in two different planes, and wherein said shaft is provided with two deflection mechanisms, each for deflecting in one of said two planes.

17. The instrument of claim 16, wherein two superposed rotary wheels are provided, which are held mechanically to one another, however, an actuation of each of the two rotary wheels can be made independently from one another.

* * * * *